United States Patent
Scholl et al.

(10) Patent No.: US 10,433,893 B1
(45) Date of Patent: Oct. 8, 2019

(54) SYSTEMS AND METHODS FOR PERFORMING SPINE SURGERY

(71) Applicant: NuVasive, Inc., San Diego, CA (US)

(72) Inventors: Thomas Scholl, San Diego, CA (US); Jeff Solimine, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 683 days.

(21) Appl. No.: 14/887,245

(22) Filed: Oct. 19, 2015

Related U.S. Application Data

(60) Provisional application No. 62/065,531, filed on Oct. 17, 2014.

(51) Int. Cl.
| | |
|---|---|
| *A61B 17/88* | (2006.01) |
| *B21D 7/02* | (2006.01) |
| *B21D 7/024* | (2006.01) |
| *B21D 7/04* | (2006.01) |
| *B21D 7/06* | (2006.01) |

(52) U.S. Cl.
CPC .......... *A61B 17/8863* (2013.01); *B21D 7/021* (2013.01); *B21D 7/024* (2013.01); *B21D 7/04* (2013.01); *B21D 7/063* (2013.01)

(58) Field of Classification Search
CPC ...... A61B 17/8863; B21D 7/02; B21D 7/021; B21D 7/024; B21D 7/04; B21D 7/14; B21D 31/005; B21D 37/02; B21D 37/04; B21D 7/06; B21D 7/063; B21D 7/066
USPC ........................... 72/458, 459, 157, 158, 159
See application file for complete search history.

(56) References Cited

U.S. PATENT DOCUMENTS

| | | | | |
|---|---|---|---|---|
| 1,964,550 | A | * 6/1934 | Abramson | ............... B21D 7/06 72/389.7 |
| 2,232,819 | A | * 2/1941 | Abramson | ............. B21D 7/063 72/217 |
| 3,018,818 | A | * 1/1962 | Swanson | .................. B21D 7/06 72/213 |
| 3,365,804 | A | 1/1968 | Fjellstrom | |
| 4,282,737 | A | 8/1981 | Maples | |
| 4,474,046 | A | 10/1984 | Cook | |
| 4,691,555 | A | * 9/1987 | Vaughan | ............... B21D 7/063 72/159 |
| 4,773,402 | A | 9/1988 | Asher | |
| 5,113,685 | A | 5/1992 | Asher | |

(Continued)

FOREIGN PATENT DOCUMENTS

| | | |
|---|---|---|
| CN | 202982181 U | 6/2013 |
| DE | 10314882 A1 | 10/2004 |

(Continued)

OTHER PUBLICATIONS

Ames, C et al., "Impact of Spinopelvic Alignment on Decision Making in Deformity Surgery in Adults: A Review," J Neurosurg Spine 16: 547-564, 2012.

(Continued)

*Primary Examiner* — Teresa M Ekiert
*Assistant Examiner* — Gregory Swiatocha

(57) ABSTRACT

A mechanical rod bender is provided for correcting a curvature or deformity in a patient's spine based on the digitized locations of implanted screws and tracking the placement of the rod as it is placed in a minimally invasive fashion. The mechanical rod bender includes a fixed die and a movable die, the movable die having multiple rod contact channels to accommodate spinal rods of different sizes.

7 Claims, 4 Drawing Sheets

(56) References Cited

U.S. PATENT DOCUMENTS

| | | | |
|---|---|---|---|
| 5,161,404 A | 11/1992 | Hayes | |
| 5,257,184 A | 10/1993 | Mushabac | |
| 5,290,289 A | 3/1994 | Sanders | |
| 5,365,996 A | 11/1994 | Crook | |
| 5,389,099 A | 2/1995 | Hartmeister | |
| 5,490,409 A | 2/1996 | Weber | |
| 5,548,985 A | 8/1996 | Yapp | |
| 5,615,572 A * | 4/1997 | Johnson | B21D 7/066 72/389.1 |
| 5,658,286 A | 8/1997 | Sava | |
| 5,672,175 A | 9/1997 | Martin | |
| 5,682,886 A | 11/1997 | Delp | |
| 5,704,937 A | 1/1998 | Martin | |
| 5,761,950 A * | 6/1998 | Chiu | B21D 7/063 72/389.1 |
| 5,768,134 A | 6/1998 | Swaelens | |
| 5,806,521 A | 9/1998 | Morimoto | |
| 5,819,571 A | 10/1998 | Johnson | |
| 5,819,580 A | 10/1998 | Gauthier | |
| 5,901,600 A | 5/1999 | Decker | |
| 6,006,581 A | 12/1999 | Holmes | |
| 6,035,691 A | 3/2000 | Lin | |
| 6,205,411 B1 | 3/2001 | Digioia, III | |
| 6,226,548 B1 | 5/2001 | Foley | |
| 6,236,875 B1 | 5/2001 | Bucholz | |
| 6,301,495 B1 | 10/2001 | Gueziec | |
| 6,327,491 B1 | 12/2001 | Franklin | |
| 6,332,780 B1 | 12/2001 | Traxel | |
| 6,347,240 B1 | 2/2002 | Foley | |
| 6,487,889 B1 * | 12/2002 | Bates | B21D 7/063 72/459 |
| 6,529,765 B1 | 3/2003 | Franck | |
| 6,578,280 B2 | 6/2003 | Kinoshita | |
| 6,644,087 B1 | 11/2003 | Ralph | |
| 6,701,174 B1 | 3/2004 | Krause | |
| 6,906,724 B2 | 6/2005 | Lake | |
| 6,978,188 B1 | 12/2005 | Christensen | |
| 7,206,626 B2 | 4/2007 | Quaid, III | |
| 7,454,939 B2 | 11/2008 | Garner | |
| 7,837,467 B2 | 11/2010 | Butscher | |
| 7,957,831 B2 * | 6/2011 | Isaacs | A61B 17/7011 623/901 |
| 8,255,045 B2 | 8/2012 | Gharib et al. | |
| 8,539,888 B2 | 9/2013 | Hernandez et al. | |
| 8,549,888 B2 * | 10/2013 | Isaacs | A61B 17/7011 72/31.04 |
| 2002/0007294 A1 | 1/2002 | Bradbury | |
| 2002/0133097 A1 | 9/2002 | Leitner | |
| 2002/0183610 A1 | 12/2002 | Foley | |
| 2003/0055435 A1 | 3/2003 | Barrick | |
| 2003/0055502 A1 | 3/2003 | Lang | |
| 2003/0149351 A1 | 8/2003 | Nowinski | |
| 2003/0205075 A1 | 11/2003 | Strippgen | |
| 2003/0215122 A1 | 11/2003 | Tanaka | |
| 2004/0068187 A1 | 4/2004 | Krause | |
| 2004/0097952 A1 | 5/2004 | Sarin | |
| 2004/0122549 A1 | 6/2004 | Otsuki | |
| 2004/0133276 A1 | 7/2004 | Lang | |
| 2004/0147927 A1 | 7/2004 | Tsougarakis | |
| 2004/0152972 A1 | 8/2004 | Hunter | |
| 2004/0158260 A1 | 8/2004 | Blau | |
| 2004/0167637 A1 | 8/2004 | Biscup | |
| 2005/0054917 A1 | 3/2005 | Kitson | |
| 2005/0101966 A1 | 5/2005 | Lavallee | |
| 2005/0119593 A1 | 6/2005 | Gallard | |
| 2005/0149050 A1 | 7/2005 | Stifter | |
| 2005/0182320 A1 | 8/2005 | Stifter | |
| 2005/0192575 A1 | 9/2005 | Pacheco | |
| 2005/0203511 A1 | 9/2005 | Wilson-MacDonald | |
| 2005/0245817 A1 | 11/2005 | Clayton | |
| 2005/0251139 A1 | 11/2005 | Roh | |
| 2005/0262911 A1 | 12/2005 | Dankowicz | |
| 2005/0288809 A1 | 12/2005 | Spaeth | |
| 2006/0005601 A1 | 1/2006 | Widmyer | |
| 2006/0015030 A1 | 1/2006 | Poulin | |
| 2006/0094951 A1 | 5/2006 | Dean | |
| 2006/0120583 A1 | 6/2006 | Dewaele | |
| 2006/0150699 A1 | 7/2006 | Garner | |
| 2006/0212158 A1 | 9/2006 | Miller | |
| 2006/0235338 A1 | 10/2006 | Pacheco | |
| 2006/0247864 A1 | 11/2006 | Tamez-Pena | |
| 2006/0264934 A1 | 11/2006 | Fallin | |
| 2006/0264973 A1 | 11/2006 | Abdelgany | |
| 2006/0282020 A1 | 12/2006 | Bertagnoli | |
| 2007/0066917 A1 | 3/2007 | Hodorek | |
| 2007/0093824 A1 | 4/2007 | Hestad | |
| 2007/0093998 A1 | 4/2007 | El-Baroudi | |
| 2007/0118055 A1 | 5/2007 | McCombs | |
| 2007/0118243 A1 | 5/2007 | Schroeder | |
| 2007/0142751 A1 | 6/2007 | Kang | |
| 2007/0198022 A1 | 8/2007 | Lang | |
| 2007/0227216 A1 | 10/2007 | Schalliol | |
| 2007/0233246 A1 | 10/2007 | Trieu | |
| 2007/0239159 A1 | 10/2007 | Altarac | |
| 2007/0250169 A1 | 10/2007 | Lang | |
| 2007/0276501 A1 | 11/2007 | Betz | |
| 2008/0009945 A1 | 1/2008 | Pacheco | |
| 2008/0039717 A1 | 2/2008 | Frigg | |
| 2008/0065067 A1 | 3/2008 | Steinberg | |
| 2008/0154120 A1 | 6/2008 | Von Jako | |
| 2008/0167547 A1 | 7/2008 | Bova | |
| 2008/0208080 A1 | 8/2008 | Ichikawa | |
| 2008/0269596 A1 | 10/2008 | Revie | |
| 2008/0269898 A1 | 10/2008 | Carls | |
| 2008/0269906 A1 | 10/2008 | Iannotti | |
| 2008/0288229 A1 | 11/2008 | Arvizo | |
| 2008/0306490 A1 | 12/2008 | Lakin | |
| 2009/0022382 A1 | 1/2009 | Feilkas | |
| 2009/0024164 A1 | 1/2009 | Neubardt | |
| 2009/0043556 A1 | 2/2009 | Axelson | |
| 2009/0082666 A1 | 3/2009 | Geist | |
| 2009/0089034 A1 | 4/2009 | Penney | |
| 2009/0093852 A1 | 4/2009 | Hynes | |
| 2009/0099605 A1 | 4/2009 | Fallin | |
| 2009/0132050 A1 | 5/2009 | Holm | |
| 2009/0149977 A1 | 6/2009 | Schendel | |
| 2009/0157083 A1 | 6/2009 | Park | |
| 2009/0157185 A1 | 6/2009 | Kim | |
| 2009/0209851 A1 | 8/2009 | Blau | |
| 2009/0209884 A1 | 8/2009 | Van Vorhis | |
| 2009/0226055 A1 | 9/2009 | Dankowicz | |
| 2009/0226068 A1 | 9/2009 | Fitz | |
| 2009/0249851 A1 | 10/2009 | Isaacs | |
| 2009/0254097 A1 | 10/2009 | Isaacs | |
| 2009/0276045 A1 | 11/2009 | Lang | |
| 2010/0030231 A1 | 2/2010 | Revie | |
| 2010/0030232 A1 | 2/2010 | Zehavi | |
| 2010/0076563 A1 | 3/2010 | Otto | |
| 2010/0100011 A1 | 4/2010 | Roche | |
| 2010/0101295 A1 | 4/2010 | Miller | |
| 2010/0111631 A1 | 5/2010 | Trieu | |
| 2010/0145663 A1 | 6/2010 | Skalli | |
| 2010/0177946 A1 | 7/2010 | De Bruijne | |
| 2010/0191071 A1 | 7/2010 | Anderson | |
| 2010/0191088 A1 | 7/2010 | Anderson | |
| 2010/0191100 A1 | 7/2010 | Anderson | |
| 2010/0234725 A1 | 9/2010 | Geist | |
| 2010/0292795 A1 | 11/2010 | Jensen | |
| 2010/0292963 A1 | 11/2010 | Schroeder | |
| 2010/0329530 A1 | 12/2010 | Lang | |
| 2010/0332197 A1 | 12/2010 | Melton | |
| 2010/0332248 A1 | 12/2010 | Pettersson | |
| 2011/0010187 A1 | 1/2011 | Andersson | |
| 2011/0015514 A1 | 1/2011 | Skalli | |
| 2011/0040340 A1 | 2/2011 | Miller | |
| 2011/0066193 A1 | 3/2011 | Lang | |
| 2011/0071802 A1 | 3/2011 | Bojarski | |
| 2011/0093023 A1 | 4/2011 | Lee | |
| 2011/0093108 A1 | 4/2011 | Ashby | |
| 2011/0094278 A1 | 4/2011 | Caporusso | |
| 2011/0107270 A1 | 5/2011 | Wang | |
| 2011/0144752 A1 | 6/2011 | Defelice | |
| 2011/0196426 A1 | 8/2011 | Peukert | |

(56) References Cited

U.S. PATENT DOCUMENTS

| | | |
|---|---|---|
| 2011/0245871 A1 | 10/2011 | Williams |
| 2011/0257653 A1 | 10/2011 | Hughes |
| 2011/0265538 A1 | 11/2011 | Trieu |
| 2011/0266265 A1 | 11/2011 | Lang |
| 2011/0268325 A1 | 11/2011 | Teichman |
| 2011/0270262 A1 | 11/2011 | Justis |
| 2011/0295378 A1 | 12/2011 | Bojarski |
| 2011/0305379 A1 | 12/2011 | Mahfouz |
| 2011/0307020 A1 | 12/2011 | Geist |
| 2011/0319745 A1 | 12/2011 | Frey |
| 2012/0010710 A1 | 1/2012 | Frigg |
| 2012/0016423 A1 | 1/2012 | Hua |
| 2012/0047980 A1 | 3/2012 | Harper |
| 2012/0063655 A1 | 3/2012 | Dean |
| 2012/0116203 A1 | 5/2012 | Vancraen |
| 2012/0141034 A1 | 6/2012 | Iannotti |
| 2012/0178069 A1 | 7/2012 | McKenzie |
| 2012/0186411 A1 | 7/2012 | Lodahi |
| 2012/0191192 A1 | 7/2012 | Park |
| 2012/0209394 A1 | 8/2012 | Bojarski |
| 2012/0230566 A1 | 9/2012 | Dean |
| 2012/0247173 A1 | 10/2012 | Paris |
| 2012/0274631 A1 | 11/2012 | Friedland |
| 2012/0290272 A1 | 11/2012 | Bryan |
| 2012/0310364 A1 | 12/2012 | Li |
| 2012/0323279 A1 | 12/2012 | Tsuang |
| 2012/0325363 A1 | 12/2012 | Knebl |
| 2013/0053854 A1 | 2/2013 | Schoenefeld |
| 2013/0072982 A1 | 3/2013 | Simonson |
| 2013/0073315 A1 | 3/2013 | Cardamone |
| 2013/0090692 A1 | 4/2013 | Nuckley |
| 2013/0091921 A1 | 4/2013 | Wilcox |
| 2013/0110174 A1 | 5/2013 | Marik |
| 2013/0123850 A1 | 5/2013 | Schoenefeld |
| 2013/0131486 A1 | 5/2013 | Copf |
| 2013/0166256 A1 | 6/2013 | Wirx-Speetjens |
| 2013/0211531 A1 | 8/2013 | Steines |
| 2013/0218163 A1 | 8/2013 | Frey |
| 2013/0238096 A1 | 9/2013 | Kotlus |
| 2013/0245803 A1 | 9/2013 | Lang |
| 2013/0268007 A1 | 10/2013 | Rezach |
| 2013/0296954 A1 | 11/2013 | Skaggs |
| 2013/0304217 A1 | 11/2013 | Recber |
| 2013/0307955 A1 | 11/2013 | Deitz |
| 2013/0325069 A1 | 12/2013 | Pereiro De Lamo |
| 2013/0332128 A1 | 12/2013 | Miles |
| 2013/0345757 A1 | 12/2013 | Stad |
| 2014/0025181 A1 | 1/2014 | Vanasse |
| 2014/0066994 A1 | 3/2014 | Dominik |
| 2014/0074438 A1 | 3/2014 | Furrer |
| 2014/0076883 A1 | 3/2014 | Brailovski |
| 2014/0081400 A1 | 3/2014 | Azernikov |
| 2014/0137618 A1 | 5/2014 | Isaacs |
| 2014/0213889 A1 | 7/2014 | Macht |
| 2014/0244220 A1 | 8/2014 | McKinnon |
| 2014/0257508 A1 | 9/2014 | Bojarski |
| 2014/0311203 A1 | 10/2014 | Crawford |
| 2014/0364916 A1 | 12/2014 | Lorio |
| 2016/0001346 A1* | 1/2016 | Holder ............. B21D 7/02 29/235 |
| 2017/0143426 A1 | 5/2017 | Isaacs et al. |

FOREIGN PATENT DOCUMENTS

| | | |
|---|---|---|
| DE | 102004008870 A1 | 10/2004 |
| EP | 1413257 A1 | 10/2002 |
| EP | 1426023 A1 | 10/2003 |
| EP | 1657681 A1 | 5/2006 |
| EP | 2017785 A1 | 1/2009 |
| EP | 2522295 A1 | 11/2012 |
| JP | 2013230221 A | 11/2013 |
| WO | WO-2003030787 A1 | 4/2003 |
| WO | WO-2004070581 A2 | 8/2004 |
| WO | WO-2006055998 A1 | 6/2006 |
| WO | WO-2007009263 A1 | 1/2007 |
| WO | WO-2008021494 A2 | 2/2008 |
| WO | WO-2008101090 A2 | 8/2008 |
| WO | WO-2008130355 A1 | 10/2008 |
| WO | WO-2009035358 A1 | 3/2009 |
| WO | WO-2009140294 A1 | 11/2009 |
| WO | WO-2010099231 A2 | 9/2010 |
| WO | WO-2012061452 A1 | 5/2012 |
| WO | WO-2012062464 A1 | 5/2012 |
| WO | WO-2012135653 A1 | 10/2012 |
| WO | WO-2012152900 A1 | 11/2012 |
| WO | WO-2013087082 A1 | 6/2013 |
| WO | WO-2013134623 A1 | 9/2013 |
| WO | WO-2013150233 A1 | 10/2013 |
| WO | WO-2014016824 A1 | 1/2014 |
| WO | WO-2013041618 A1 | 3/2014 |
| WO | WO-2014037093 A1 | 3/2014 |
| WO | WO-2014048448 A1 | 4/2014 |
| WO | WO-2014070889 A1 | 5/2014 |
| WO | WO-2014079812 A1 | 5/2014 |
| WO | WO-2014088801 A1 | 6/2014 |
| WO | WO-2014107144 A1 | 7/2014 |

OTHER PUBLICATIONS

Aubin, C et al., "Preoperative Planning Simulator for Spinal Deformity Surgeries," Spine vol. 33, No. 20, pp. 2143-2152, 2008.

Langlotz et al. "A Pilot Study on Computer-Assisted Optimal Contouring of Orthopedic Fixation Devices". Computer Aided Surgery vol. 4 (1999): 305-313.

Le Huec, J et al., "Equilibrium of the Human Body and the Gravity Line: The Basics," Eur Spine J (2011) 20 (Suppl 5):S558-S563.

Roussouly, P et al., "Sagittal Parameters of the Spine: Biomechanical Approach," Eur Spine J (2011) 20 (Suppl 5):S578-S585.

Schwab, F et al., "Adult Spinal Deformity—Postoperative Standing Imbalance, How Much Can You Tolerate? An Overview of Key Parameters in Assessing Alignment and Planning Corrective Surgery," Spine vol. 35, No. 25, 2224-2231, 2010.

Terran, J et al., "The SRS-Schwab Adult Spinal Deformity Classification: Assessment and Clinical Correlations Based on a Perspective Operative and Nonoperative Cohort," Neurosurgery 73: 559-568, 2013.

Goodrich and Volcan, eds., "Spinal Alignment and Correction in Adults," eXtreme Lateral Interbody Fusion (XLIF®), $2^{nd}$ Edition, 2013, Chapter 9, 91-115, Quality Medical Publishing, Inc., St. Louis, Missouri.

* cited by examiner

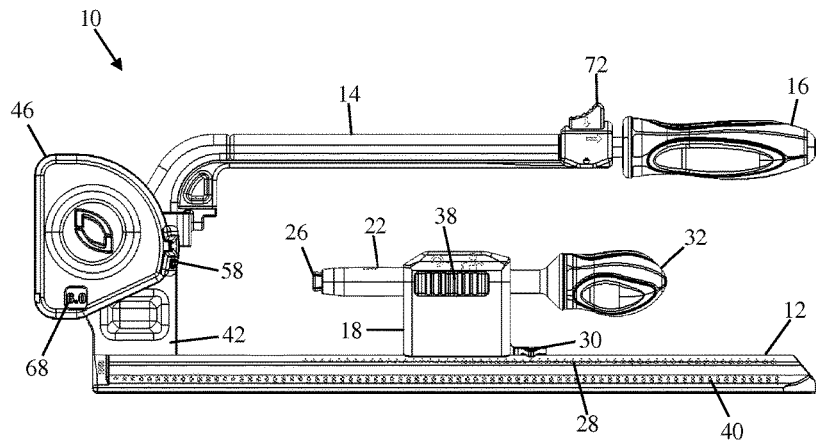
Fig. 3
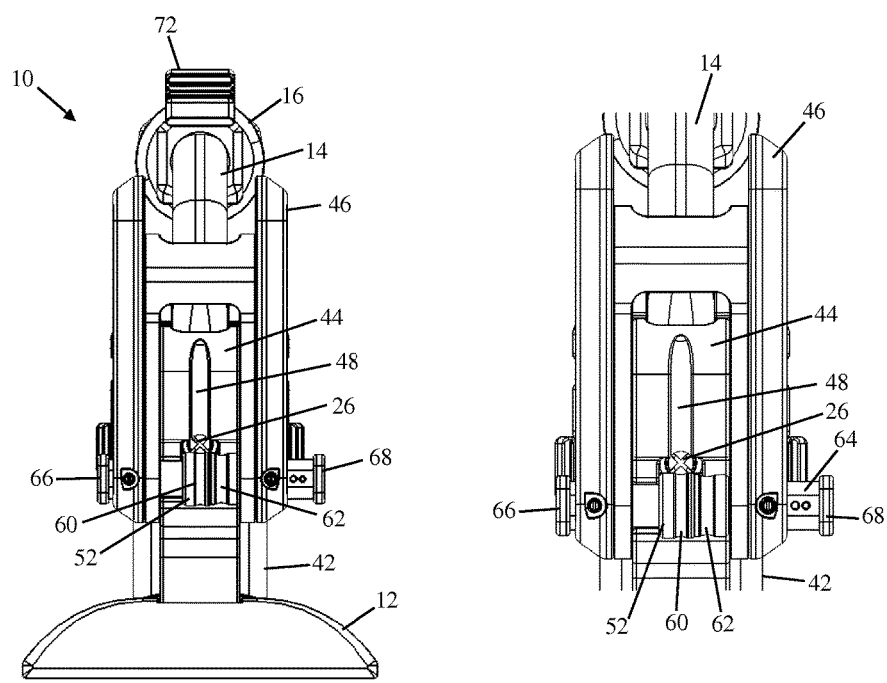
Fig. 4
Fig. 5

SYSTEMS AND METHODS FOR PERFORMING SPINE SURGERY

CROSS-REFERENCE TO RELATED APPLICATIONS

This application claims priority to U.S. Provisional Application Ser. No. 62/065,531 filed on Oct. 17, 2014 and entitled "Systems and Methods of Performing Spine Surgery," the complete disclosure of which is hereby incorporated by reference into this application as if set forth fully herein.

FIELD

The present application pertains to spine surgery. More particularly, the present application pertains to systems and methods related to the planning, design, formation, and implantation of spinal implants.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

Screws, hooks, and rods are devices used to stabilize the spine during a spinal fixation procedure. Such procedures often require the instrumentation of many bony elements. The devices, for example rods, can be extremely challenging to design and implant into the patient. Spinal rods are usually formed of stainless steel, titanium, cobalt chrome, or other similarly hard metal, and as such are difficult to bend without some sort of leverage-based bender. Moreover, a spinal rod needs to be oriented in six degrees of freedom to compensate for the anatomical structure of a patient's spine as well as the attachment points (screws, hooks) for securing the rod to the vertebrae. Additionally, the physiological problem being treated as well as the physician's preferences will determine the exact configuration necessary. Accordingly, the size, length, and particular bends of the spinal rod depends on the size, number, and position of each vertebrae to be constrained, the spatial relationship amongst vertebrae, as well as the screws and hooks used to hold the rods attached to the vertebrae.

The bending of a spinal rod can be accomplished by a number of methods. The most widely used method is a three-point bender called a French Bender. The French bender is a pliers-like device that is manually operated to place one or more bends in a rod. The French bender requires both handles to operate and provides leverage based on the length of the handle. The use of the French bender requires a high degree of physician skill because the determination of the location, angle, and rotation of bends is often subjective and can be difficult to correlate to a patient's anatomy. Other methods of bending a rod to fit a screw and/or hook construct include the use of an in-situ rod bender and a keyhole bender. However, all of these methods can be subjective, iterative, and are often referred to as an "art." As such, rod bending and reduction activities can be a time consuming and potentially frustrating step in the finalization of a complex and/or long spinal construct. Increased time in the operating room to achieve optimum bending can be costly to the patient and increase the chance of the morbidity. When rod bending is performed poorly, the rod can preload the construct and increase the chance of failure of the fixation system. The bending and re-bending involved can also promote metal fatigue and the creation of stress risers in the rod.

Efforts directed to computer-aided design or shaping of spinal rods have been largely unsuccessful due to the lack of bending devices as well as lack of understanding of all of the issues involved in bending surgical devices. U.S. Pat. No. 7,957,831, issued Jun. 7, 2011 to Isaacs, describes a rod bending system which includes a spatial measurement subsystem with a digitizer to obtain the three dimensional location of surgical implants (screws, hooks), software to convert the implant locations to a series of bend instructions, and a mechanical rod bender used to execute the bend instructions such that the rod will be bent precisely to custom fit within each of the screws. This is advantageous because it provides quantifiable rod bending steps that are customized to each patient's anatomy enabling surgeons to create custom-fit rods on the first pass, thereby increasing the speed and efficiency of rod bending, particularly in complex cases. This, in turn, reduces the morbidity and cost associated with such procedures. However, a need still exists for improved rod bending systems that allow for curvature and deformity correction in fixation procedures, provide the user with more rod bending options, and accommodate more of the user's clinical preferences including the ability to determine the spatial orientation of the tip of the rod and the tip of the rod pusher relative to one another.

Commercially-available benders currently use only one channel for rods. Benders that can accommodate multiple sizes do so by opening the mandrel and roller (moving die) to the required size. Although many benders can accommodate multiple rods, their geometry may only be ideal for one size or may be broad and not be particularly ideal for any size. If a rod with a diameter larger than the channel gets bent using these benders, notching will occur on the two contacting points lengthwise on the rod. If a smaller than ideal rod is used, the rod will be more flat on bent surfaces. If a larger than ideal rod is used, it can also create notching or depression across the width of the rod due to smaller surface contact. The rod bender described below overcomes these disadvantages by providing multiple-sized rod channels and, in doing so, affords the user the ability to create more acute bend angles on multiple sized rods with the same bender. It also reduces non-desired deformation (depressions, flattening, notching) in rod by distributing the forces on the rod more evenly.

SUMMARY

The present disclosure describes a rod bender that enables a user (e.g., surgeon) to customize bending of a spinal rod to suit the desired correction of a patient's spinal condition. According to a broad aspect, the rod bender includes a base and a lever with a lever handle designed for grabbing the lever manually. The lever is maneuverable relative to the base, which acts as a static second lever. The base further includes a slide block slideably coupled with the base by way of a slide track. The slide block has a rod holder including a rod pass through configured to accommodate an infinitely long rod as well as steady the rod during the bending process. A collet on the distal end of the rod holder holds the rod in place relative to the rod holder. By sliding slide block along the base, the rod can be moved proximally and distally within the mechanical rod bender. The rod holder further includes a collet knob that is rotatable (both clockwise and counterclockwise) by a user to set a particular rotation angle. The rod holder further includes rotation interval markings to give the user a visual indication of the degree of rotation. When turning the collet knob, the user can set the collet knob at a particular interval marking or in between several interval markings to determine a particular angle rotation to a high degree of accuracy. The slide block further includes a lock switch that toggles between an unlocked position that allows free rotation of the collet handle (and associated rod) and a locked position that prevents rotation of the collet handle (and associated rod) during bending.

The rod bender further includes a fulcrum block positioned at the distal end of the base. The fulcrum block includes a fixed die and a housing. The fixed die includes a first rod channel. The housing is pivotally coupled with the fulcrum block and includes an angle gauge and a moveable die. The bend angle is measured by using angle gauge. The angle gauge has ratchet teeth spaced at regular intervals. By way of example, each ratchet stop represents five degrees of bend angle with the particular bend angle gauge as the lever is opened and closed. However, it is to be appreciated that each ratchet step may represent any suitable degree increment (e.g., between 0.25 degrees to 10 degrees). The angle gauge may further include a series of angle markings and an angle indicator that gives the user visual feedback about the bend angle.

The moveable die is positioned at one end of the housing and moves relative to the base (and fixed die) when the housing is caused to pivot about the fulcrum block during use. This movement ultimately effects the desired bend in the rod. The moveable die includes multiple rod channels. Each rod channel has a diameter and height specific to a corresponding rod size. The first rod channels are positioned parallel to one another. The moveable die can be actuated with a switch to align the desired rod channel with the rod channel on the fixed die. By way of example, the actuation switch includes buttons positioned on either side of the moveable die. Alternate implementations for the actuation switch are also contemplated and are within the scope of this disclosure. The user may input the appropriate rod diameter by pressing the button corresponding to the diameter of the rod to be bent and implanted into the patient. The moveable die then slides into appropriate bending position by aligning one of the rod channels with the rod channel on the fixed die. One or more mechanisms may be employed to maintain the moveable die in the desired position. The rod bender is then ready to bend the surgical rod.

The lever is pivotally coupled to the fulcrum block and is able to pivot independently of the housing. The distal end of the lever includes ratchet teeth configured to engage the ratchet teeth of the angle gauge to enable the lever to be manipulated to cause the housing to pivot.

Additional bends can be formed in the rod without removing the from the rod holder. The user can translate the slide block and/or rotate the collet knob without adjusting the position of the rod within the rod holder to alter the position of the spinal rod relative to the fixed die and moveable die. Alternatively, the rod may be adjusted relative to the rod holder prior to effecting additional bends in the rod. Once all the desired bends are formed in the rod, the user removes the spinal rod from the rod holder.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 3 is a side plan view of the mechanical rod bender of FIG. 1;

FIG. 4 is a front plan view of the mechanical rod bender of FIG. 1;

FIG. 5 is a close-up view of the front of the mechanical rod bender of FIG. 1;

DESCRIPTION OF THE PREFERRED EMBODIMENT

Figure 1:
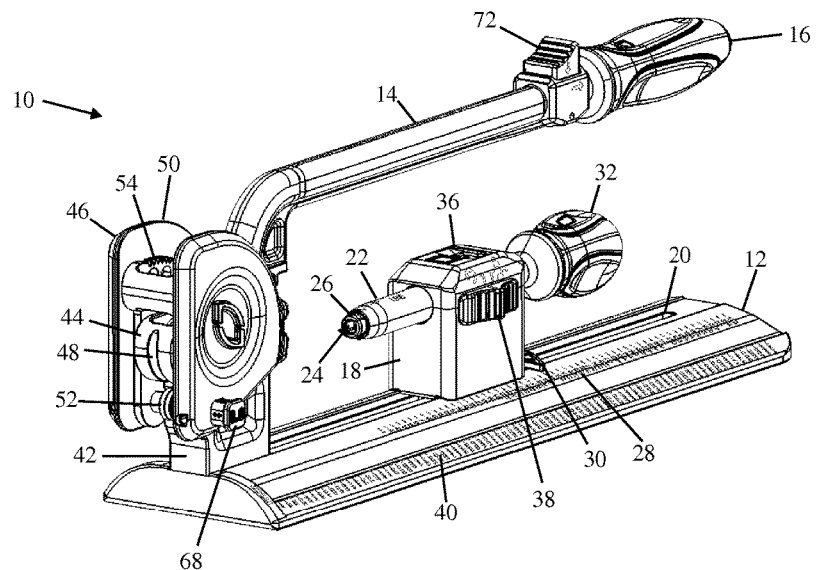
FIG. 1 is a perspective view of a mechanical rod bender according to one embodiment.
Figure 2:
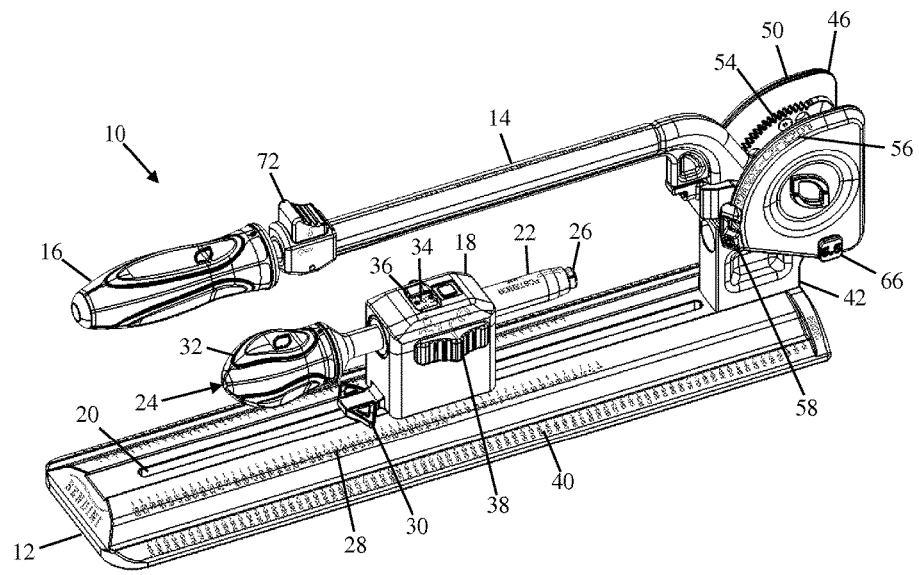
FIG. 2 is an alternative perspective view of the mechanical rod bender of FIG. 1.

Illustrative embodiments of the invention are described below. In the interest of clarity, not all features of an actual implementation are described in this specification. It will of course be appreciated that in development of any such actual embodiment, numerous implantation-specific decisions must be made to achieve the developers' specific goals such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

The accompanying FIGS. 1-9 illustrate an example of a mechanical rod bender 10 according to one embodiment. The mechanical rod bender 10 of the present disclosure is configured to be used as part of a surgical bending system, for example the surgical bending systems shown and described in commonly-owned U.S. Pat. No. 8,539,888, issued Oct. 8, 2013 and entitled "System and Device for Designing and Forming a Surgical Implant," and commonly-owned and co-pending U.S. patent application Ser. No. 13/815,643, filed Mar. 12, 2013 and entitled "System and Method for Performing Spinal Surgery," the entire contents of each of which are hereby incorporated by reference into this disclosure as if set forth fully herein. In addition to a mechanical rod bender, the surgical bending systems described in the '888 patent and '643 application also include a spatial tracking system to obtain the location of one or more surgical implants and a control unit containing software to convert the implant locations to a series of bend instructions. The mechanical rod bender 10 of the present disclosure differs from the examples described in the incorporated references in that it includes multiple sized rod channels to accommodate respective rod sizes.

Generally, the spatial tracking system includes an IR sensor, a digitizer pointer, as well as other components including Host USB converter. The spatial tracking system is in communication with control unit. The control unit has spatial relation software and is communicatively linked to the display so that information relevant to the surgical procedure may be conveyed to the user in a meaningful manner. By way of example, the relevant information includes, but is not limited to, spatial positioning data acquired by the IR sensor (e.g., translational data in the x, y, and z axes and orientation/rotational data $R_x$, $R_y$, and $R_z$). A neuromonitoring system may be communicatively linked to the spatial tracking system via the control unit. By way of example only, the neuromonitoring system may be the neuromonitoring system shown and described in U.S. Pat. No. 8,255,045, entitled "Neurophysiologic Monitoring System" and filed on Apr. 3, 2008, the entire contents of which are hereby incorporated by reference as if set forth fully herein. Once the user has selected the desired rod solution, the user then executes the bends using a mechanical rod bender 10. The mechanical rod bender 10 takes into account six degrees of freedom information as it effects bends onto a spinal rod.

FIGS. 1-7 illustrate an example of a rod bender 10 having multiple rod channels according to one implementation. By way of example, the rod bender 10 includes a base 12 and a lever 14 including a lever handle 16 designed for grabbing the lever 14 manually. The lever 14 is maneuverable relative to the base 12, which acts as a static second lever. The base further includes a slide block 18 slideably coupled with the base 12 by way of a slide track 20. The slide block 18 further has a rod holder 22 including a rod pass through 24 configured to accommodate an infinitely long rod as well as steady the rod during the bending process. A collet 26 on the distal end of the rod holder 22 holds the rod in place relative to the rod holder 22. By sliding slide block 18 along the base 12, the rod can be moved proximally and distally within the mechanical rod bender 10. The position of the rod may be measured by click stops 28 (or other markings) positioned at regular intervals along base 12 on either side of the slide track 20. Each click stop 28 is a measured distance along the base 12 and thus moving a specific number of click stops 28 gives one a precise location for the location of a desired rod bend. A location indicator 30 is attached to the slide block 18 and functions to indicate the precise click stop 28 at which the slide block 18 is located. The rod holder 22 further includes a collet knob 32 that is rotatable (both clockwise and counterclockwise) by a user to set a particular rotation angle. The rod holder 22 further includes rotation interval markings 34 to give the user a visual indication of the degree of rotation. When turning the collet knob 32, the user can set the collet knob 32 at a particular interval marking 34 or in between several interval markings 34 to determine a particular angle rotation to a high degree of accuracy. The rotation interval markings 34 may be located on any portion of the rod holder 22 and/or collet knob 32. In the example shown in FIG. 2, the rotation interval markings 34 are located on a portion of the rod holder 22 that extends through the slide block 18, and therefore are viewable through an aperture 36 formed within the slide block 18. The slide block 18 further includes a lock switch 38 that toggles between an unlocked position that allows free rotation of the collet handle 32 (and associated rod) and a locked position that prevents rotation of the collet handle 32 (and associated rod) during bending. Additionally the base 12 may have ruler-type markings 40 along its length to aid the user in measuring a rod intraoperatively.

The rod bender 10 further includes a fulcrum block 42 positioned at the distal end of the base 12. The fulcrum block 42 includes a fixed die 44 and a housing 46. The fixed die 44 includes a first rod channel 48. The housing 46 is pivotally coupled with the fulcrum block 42 and includes an angle gauge 50 and a moveable die 52. The bend angle is measured by using angle gauge 50. The angle gauge 50 has ratchet teeth 54 spaced at regular intervals. By way of example, each ratchet stop represents five degrees of bend angle with the particular bend angle gauge 50 as the lever 14 is opened and closed. However, it is to be appreciated that each ratchet step may represent any suitable degree increment (e.g., between 0.25 degrees to 10 degrees). The angle gauge 50 may further include a series of angle markings 56 and an angle indicator 58 that gives the user visual feedback about the bend angle.

The moveable die 52 is positioned at one end of the housing 46 and moves relative to the base 12 (and fixed die 44) when the housing 46 is caused to pivot about the fulcrum block 42 during use. This movement ultimately effects the desired bend in the rod. As best viewed in FIGS. 4-7, the moveable die 52 includes multiple rod channels, for example first and second rod channels 60, 62. It is possible that the moveable die 52 may include additional rod channels without departing from the scope of this disclosure. Each rod channel 60, 62 has a diameter and height specific to a corresponding rod size. By way of example only, the first rod channel 60 is sized to accommodate 5.5 mm rods, and the second rod channel 62 is sized to accommodate 6.0 mm rods. However, first and second rod channels 60, 62 (and/or any additional rod channels) may be sized to accommodate rods of any particular diameter. The first and second rod channels 60, 62 are positioned parallel to one another. The moveable die 52 can be actuated with a switch 64 to align the desired rod channel 60, 62 with the rod channel 48 on the fixed die 44. By way of example, the actuation switch 64 includes first and second buttons 66, 68 positioned on either side of the moveable die 52. Alternate implementations for the actuation switch are also contemplated and are within the scope of this disclosure. The user may input the appropriate rod diameter by pressing the button corresponding to the diameter of the rod to be bent and implanted into the patient. The moveable die 52 then slides into appropriate bending position by aligning one of the first and second rod channels 60, 62 with the rod channel 48 on the fixed die 44.

Figure 6:
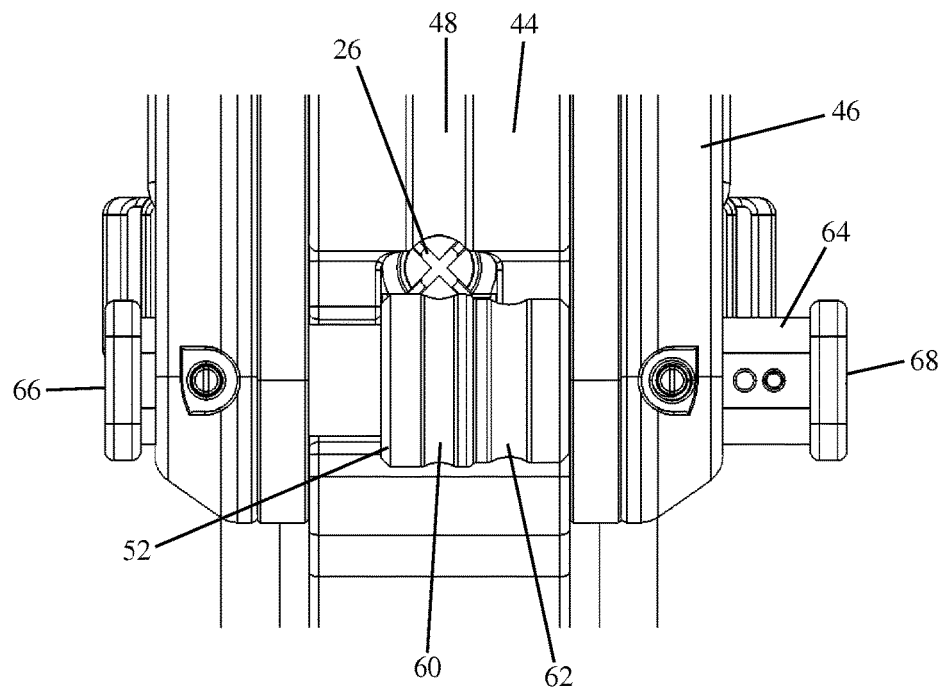
FIG. 6 is a further close-up view of the front of the mechanical rod bender of FIG. 1 with the actuation switch in a first position.
Figure 7:
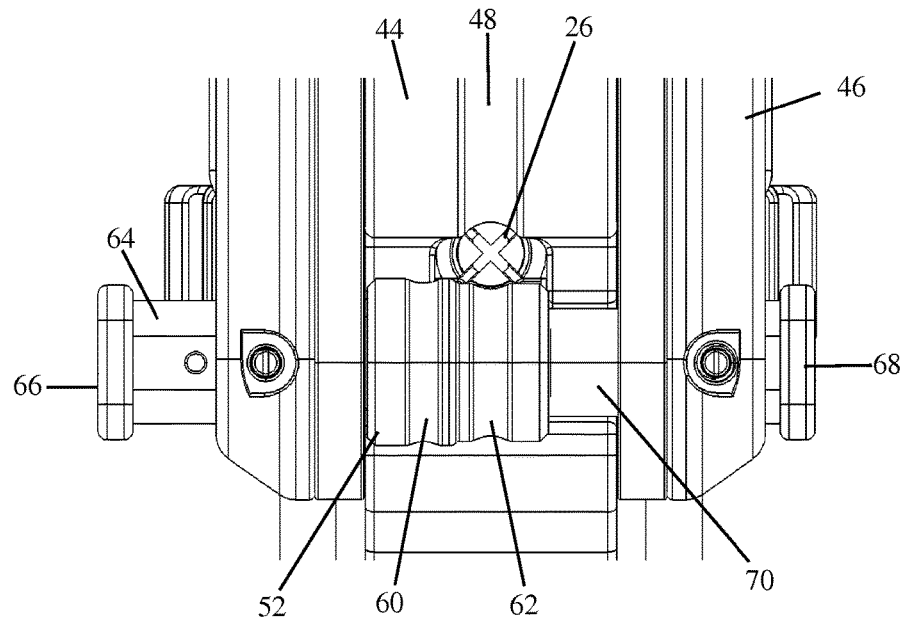
FIG. 7 is a further close-up view of the front of the mechanical rod bender of FIG. 1 with the actuation switch in a second position.

For example, when the first button 66 is depressed, the moveable die 52 is positioned such that the first rod channel 60 is aligned with the rod channel 48 on the fixed die 44 (FIG. 6). When the second button 68 is depressed, the moveable die 52 is positioned such that the second rod channel 62 is aligned with the rod channel 48 on the fixed die 44 (FIG. 7). One or more mechanisms may be employed to maintain the moveable die 52 in the desired position. As shown in FIG. 7, a cap 70 may extend from the second button 68 through an aperture in the housing 46 (not shown). When the second button 68 is fully depressed, the cap 70 is maximally positioned adjacent the moveable die 52 such that the moveable die 52 is prohibited from translating laterally once the channel size is selected. The rod bender 10 is then ready to bend the surgical rod.

The lever 14 is pivotally coupled to the fulcrum block 42 and is able to pivot independently of the housing 46. The distal end of the lever 14 includes ratchet teeth (not shown) configured to engage the ratchet teeth 54 of the angle gauge 50 to enable the lever 14 to be manipulated to cause the housing 46 to pivot.

Figure 8:
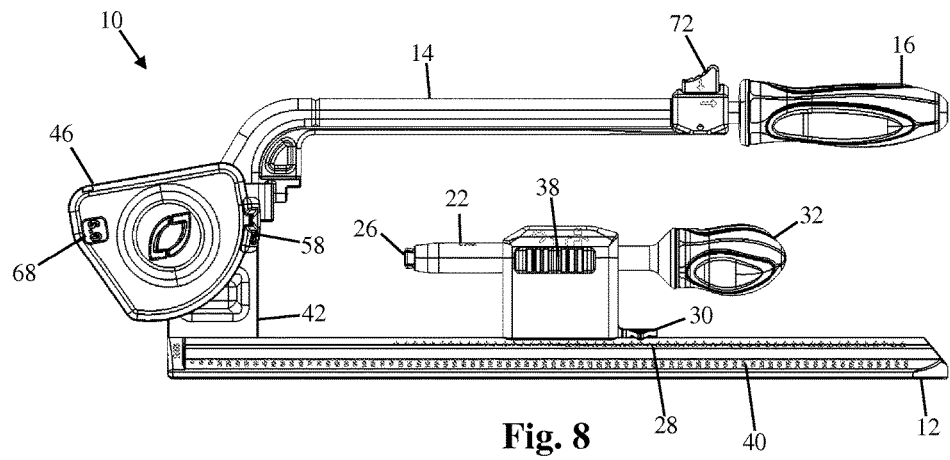
FIG. 8 is a side plan view of the mechanical rod bender of FIG. 1 after bending of a spinal rod.
Figure 9:
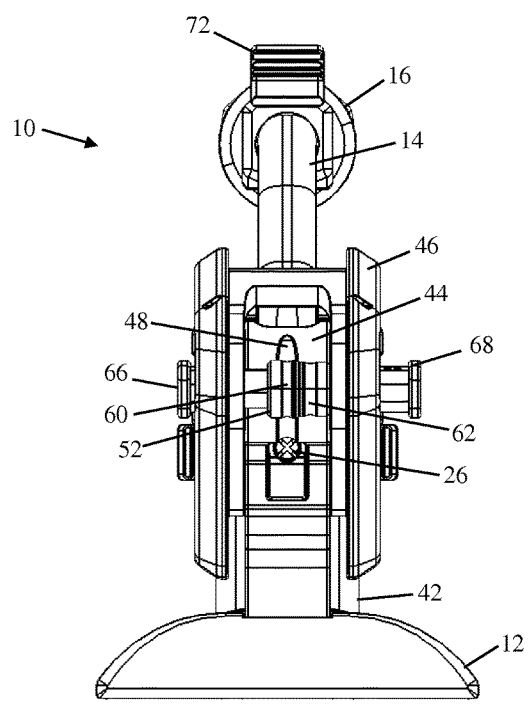
FIG. 9 is a front plan view of the mechanical rod bender of FIG. 1 after bending of a spinal rod.

To use the rod bender 10 of the present disclosure, a user first selects the appropriate spinal rod for the procedure. For the purpose of illustration, the user may select a 5.5 mm spinal rod. Once a 5.5 mm rod is selected, the user ensures that the first button 66 is depressed thus aligning the first rod channel 60 (configured for a 5.5 mm rod in the present example) of the moveable die 52 with the rod channel 48 of the fixed die 44. The spinal rod is inserted longitudinally through the rod pass through 24 of the rod holder 22, and further inserted distally such that a portion of the spinal rod interacts with both the rod channel 48 of the fixed die 44 and the first rod channel 60 of the moveable die 52. The user then manually engages the lever handle 16 and pivots the lever 14 away from the base 12. As the lever 14 is pivoting, the lever ratchet teeth positively engage the ratchet teeth 54 on the angle gauge 50. Once the lever 14 has been pivoted to the point where the desired angle marking 56 is shown within the angle indicator 58, the user then closes the handle 16 (by exerting a downward force on the lever 14) such that the lever 14 and base 12 are brought closer together. The rod is bent between the fixed die 44 and the moveable die 52. The mechanical rod bender 10 could be modified to bend the rod during the handle opening movement as well, as shown with other embodiments shown and described in the above-referenced '888 patent and/or '643 application. Various gauges on the rod bender 10 allow the user to manipulate the rod in order to determine bend position, bend angle, and bend rotation. FIGS. 8 and 9 illustrate the relative positioning of the housing 50, as well as the fixed die 44 and moveable die 52 after the rod has been bent. The rod bender 10 may be reset to the original position by engaging a release button 72 near the lever handle 16. The release button 72 causes the lever ratchet teeth to disengage from the ratchet teeth 54, enabling the housing 50 to be rotated back to the initial position.

Additional bends can be formed in the rod without removing the from the rod holder 22. The user can translate the slide block 18 and/or rotate the collet knob 32 without adjusting the position of the rod within the rod holder 22 to alter the position of the spinal rod relative to the fixed die 44 and moveable die 52. Alternatively, the rod may be adjusted relative to the rod holder 22 prior to effecting additional bends in the rod. Once all the desired bends are formed in the rod, the user removes the spinal rod from the rod holder 22.

The rod bender 10 of the present application may include additional features shown and described in the above-referenced '888 patent and/or the '643 application without departing from the scope of the present disclosure. For example, the rod bender 10 may be a pneumatic or motor-driven device that automatically adjusts the location, rotation and bend angle of the rod. The bend calculations could be converted into an interface program that would run to power and control the motors. The automated bender would lessen the possibility of user error in following the manual bend instructions. It would also increase the resolution or number of bends that can be imparted in the rod making for a smoother looking rod.

While the invention is susceptible to various modifications and alternative forms, specific embodiments thereof have been shown, by way of example only, in the drawings and are herein described in detail. It should be understood, however, that the description herein of specific embodiments is not intended to limit the invention to the particular forms disclosed. On the contrary, the invention is to cover all modifications, equivalents, and alternatives falling within the spirit and scope of the invention as defined herein.

What is claimed is:

1. A device for effecting at least one bend in a spinal rod, comprising:
    a fixed die having a first spinal rod contacting surface;
    a moving die having a first rod channel including a second spinal rod contacting surface and a second rod channel including a third spinal rod contacting surface, the first rod channel sized to accommodate a portion of a first spinal rod having a first diameter, the second rod channel sized to accommodate a portion of a second spinal rod having a second diameter that is different than the first diameter, the moving die spaced apart from the fixed die to receive the first spinal rod or the second spinal rod between the fixed die and moving die;
    an actuation switch coupled to the moving die, wherein the actuation switch comprises a first button and a second button, wherein the first button and the second button are positioned on opposite sides of the moveable die along an axis, wherein depression of the first button or the second button enables a translation of the moving die along the axis between (i) a first position in which the second spinal rod contacting surface is in alignment with the first spinal rod contacting surface and (ii) a second position in which the third spinal rod contact surface is in alignment with the first spinal rod contacting surface;
    an elongated base member supporting the fixed die;
    a housing member supporting the moving die and pivotably engaged to the elongated base member; and
    an elongated pivot member pivotably engaged to the elongated base member and releasably engageable to the housing member to pivot the moving die relative to the fixed die to impart a bend to the spinal rod upon pivoting of the moving die.

2. The device of claim 1, further including an angle gauge positioned on the housing member, the housing member configured for initially supporting the elongated pivot member relative to the elongated base member in one of a plurality of pre-determined angular positions, wherein the one of the plurality of pre-determined angular positions is determined according to the angle gauge.

3. The device of claim 2, wherein the angle gauge includes a plurality of ratchet teeth.

4. The device of claim 3, wherein the elongated pivot member is releasably engageable to the housing member by interacting with the ratchet teeth of the angle gauge.

5. The device of claim 1, further comprising a clamp member mounted to the elongated base member and configured to engage the spinal rod with the rod in position between the fixed and moving dies.

6. The device of claim 5, wherein the clamp member is translatable along at least a portion of the length of the elongated base.

7. The device of claim 5, wherein the clamp member includes a knob configured to rotate the clamp about a longitudinal axis of the spinal rod to a pre-determined angular orientation.

* * * * *